United States Patent
Witt-Enderby et al.

(10) Patent No.: US 8,785,501 B2
(45) Date of Patent: Jul. 22, 2014

(54) ANTI-CANCER TAMOXIFEN-MELATONIN HYBRID LIGAND

(75) Inventors: Paula A. Witt-Enderby, Bethel Park, PA (US); Vicki L. Davis, Seven Fields, PA (US); David Lapinsky, Allison Park, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 76 days.

(21) Appl. No.: 13/497,954

(22) PCT Filed: Oct. 12, 2010

(86) PCT No.: PCT/US2010/002726
§ 371 (c)(1),
(2), (4) Date: May 23, 2012

(87) PCT Pub. No.: WO2011/046596
PCT Pub. Date: Apr. 21, 2011

(65) Prior Publication Data
US 2013/0072539 A1   Mar. 21, 2013

Related U.S. Application Data

(60) Provisional application No. 61/278,875, filed on Oct. 13, 2009.

(51) Int. Cl.
*A01N 33/02* (2006.01)
*A61K 31/135* (2006.01)
*A01N 43/38* (2006.01)
*A61K 31/405* (2006.01)

(52) U.S. Cl.
USPC ............................. 514/651; 514/415

(58) Field of Classification Search
USPC ........................................... 514/651
See application file for complete search history.

(56) References Cited

U.S. PATENT DOCUMENTS

| | | | |
|---|---|---|---|
| 6,090,800 A * | 7/2000 | Unger et al. | 514/180 |
| 2005/0074425 A1 | 4/2005 | Waugh et al. | |
| 2005/0208139 A1 | 9/2005 | Hilt et al. | |
| 2008/0050413 A1 | 2/2008 | Horvers et al. | |

OTHER PUBLICATIONS

Kothari, A., et al., "Combination of melatonin . . . rat mammary tumors," Cancer Letters 111, 59-66, 1997.
Lissoni, P., et al., "Modulation of cancer endocrine therapy . . . tamoxifen alone," British Journal of Cancer, 71, 854-856, 1995.
Witt-Enderby, Paula A., et al., "Therapeutic treatments . . . adjuvant therapy," J. Pineal Res., 41, 297-305, 2006.
Grant, S., et al., "Melatonin and breast cancer . . . future perspectives," Expert Reviews in Molecular Medicine, 11, e5, 1-15, 2009.
Kisanga, E., et al., "Tamoxifen and metabolite concentrations . . . preoperative trial," Clinical Cancer Research, 10, 2336-2343, 2004.
Lissoni, P., et al., "A phase II study of tamoxifen plus melatonin in metastatic solid tumour patients," British Journal of Cancer, 1996, 74, 1466-1468.
Rodriguez-Franco, Maria Isabel et al., "Novel Tacrine-Melatonin Hybrids as Dual-Acting Drugs for Alzheimers Disease, with Improved Acetylcholinesterase Inhibitory and Antioxidant Properties," J. Med. Chem, 2006, 49, 459-462.
Shan, Min et al., "Nonsteroidal Bivalent Estrogen Ligands: An Application of the Bivalent Concept to the Estrogen Receptor," ACS Chemical Biology, 2013, 8, 707-715.

* cited by examiner

*Primary Examiner* — Layla Soroush
(74) *Attorney, Agent, or Firm* — Barbara E. Johnson, Esq.

(57) ABSTRACT

A particularly constructed tamoxifen-melatonin hybrid ligand gives new and unexpectedly improved results in the prevention and treatment of cancer, particularly breast cancer. The hybrid ligand comprises either tamoxifen or 4-hydroxytamoxifen and also melatonin, with the tamoxifen or 4-hydroxytamoxifen and melatonin's being linked by an unsubstituted $C_2$-$C_6$ alkyl linker between the tamoxifen amine and the carbonyl of melatonin.

5 Claims, 8 Drawing Sheets

ANTI-CANCER TAMOXIFEN-MELATONIN HYBRID LIGAND

CROSS REFERENCE TO RELATED APPLICATION

This patent application claims priority to, and incorporates herein by reference, U.S. Provisional Patent Application No. 61/278,875 filed 13 Oct. 2009.

BACKGROUND OF THE INVENTION

1. Field of the Invention

Two previously known active agents are covalently linked into a particularly constructed hybrid ligand for preventing or treating cancer in animals or humans, particularly breast cancer in mammals.

2. Description of Related Art

Both tamoxifen and melatonin are known active agents; both are also known for certain anti-cancer effects. Tamoxifen is already known in the prior art to treat: a) women diagnosed with hormone-receptor-positive, early-stage breast cancer post procedure, to reduce recurrence; and b) women and men diagnosed with metastatic hormone-receptor-positive disease to produce regression and remission. Indeed, at this writing Tamoxifen is the world's largest selling drug for the treatment of breast cancer. Tamoxifen is also given at this writing to women who have not been diagnosed with breast cancer but whom are at higher-than-average risk for disease. It is generally accepted at this writing that Tamoxifen is not useful in treating hormone-receptor-negative breast cancer.

Melatonin has increasingly been understood as relevant to breast cancer in various ways. Certain studies show that as melatonin levels reduce after about age 40, risk for breast cancer also increases. Moreover, patient assays and laboratory experiments indicate both that lower levels of melatonin stimulate growth of breast cancer cells and that adding melatonin to these cells inhibits their growth. Daily melatonin administration has been shown in some studies to increase survival time of laboratory animals having untreated mammary tumors. Animals with mammary tumors also exhibited increased levels of prolactin and catecholamine concentrations compared to the healthy animals, and the administration of melatonin stabilized the hormone levels—returning the levels to those of healthy animals and suggesting that melatonin administration is therapeutic to hormone-receptor-positive cancer.

At this writing, however, experts in oncology generally agree that despite their significant benefits, neither tamoxifen nor melatonin presents an adequate active agent for preventing or treating hormone-receptor-related cancer taken alone. Breast cancer is currently the second leading cause of cancer deaths in women today. Excluding nonmelanoma skin cancers, breast cancer remains the most common cancer among women. According to the American Cancer Society, about 1.3 million women worldwide will be diagnosed annually with breast cancer and 465,000 will die of the disease. Accordingly, a need remains for a prevention and treatment approach that improves on available products and therapies.

SUMMARY OF THE INVENTION

In order to meet this need, the present invention is a particularly constructed tamoxifen-melatonin hybrid ligand that gives new and unexpectedly improved results in the prevention and treatment of cancer, particularly breast cancer. The hybrid ligand comprises either N-desmethyl tamoxifen or N-desmethyl 4-hydroxytamoxifen and also melatonin, with the N-desmethyl tamoxifen or N-desmethyl 4-hydroxytamoxifen and melatonin being linked by a substituted or unsubstituted $C_2$-$C_6$ alkyl linker between the tamoxifen amine and the carbonyl of melatonin. Throughout the specification and claims, "tamoxifen" and "4-hydroxytamoxifen" should be understood to be N-desmethyl tamoxifen and N-desmethyl 4-hydroxytamoxifen, respectively. A $C_5$ alkyl linker is preferred. The hybrid ligand may be administered together with pharmaceutically acceptable excipients and diluents in solution, tablet, capsule, caplet, powder, suspension, transdermal, transmucosal or other dosage form via routes of administration including but not limited to parenteral, oral, transmucosal and transdermal, with oral and parenteral administration being preferred.

BRIEF DESCRIPTION OF THE DRAWING(S)

FIG. 4($a$) is a line graph showing Competition of Tamoxifen for $[^{125}I]$ Estradiol Binding to Estrogen Receptors (ERs) Expressed in Mouse Uterus FIG. 4($b$) is a line graph showing Competition of the present Hybrid Ligand (HL) for $[^{125}I]$ Estradiol Binding to ERs Expressed in Mouse Uterus FIG. 4($c$) is a line graph showing Competition of Melatonin for $[^{125}I]$ iodomelatonin Binding to Human $MT_1Rs$ FIG. 4($d$) is a line graph showing Competition of HL for $[^{125}I]$ iodomelatonin Binding to Human $MT_1Rs$.

FIG. 5($a$) is a set of two line graphs showing comparative data for ERs in Mouse Uterus FIG. 5($b$) is a set of two line graphs showing comparative data for ERs in Mouse Uterus FIG. 5($c$) is a set of two line graphs showing comparative data for Human $MT_1Rs$ in CHO cells.

DETAILED DESCRIPTION OF THE INVENTION

Figure 1:
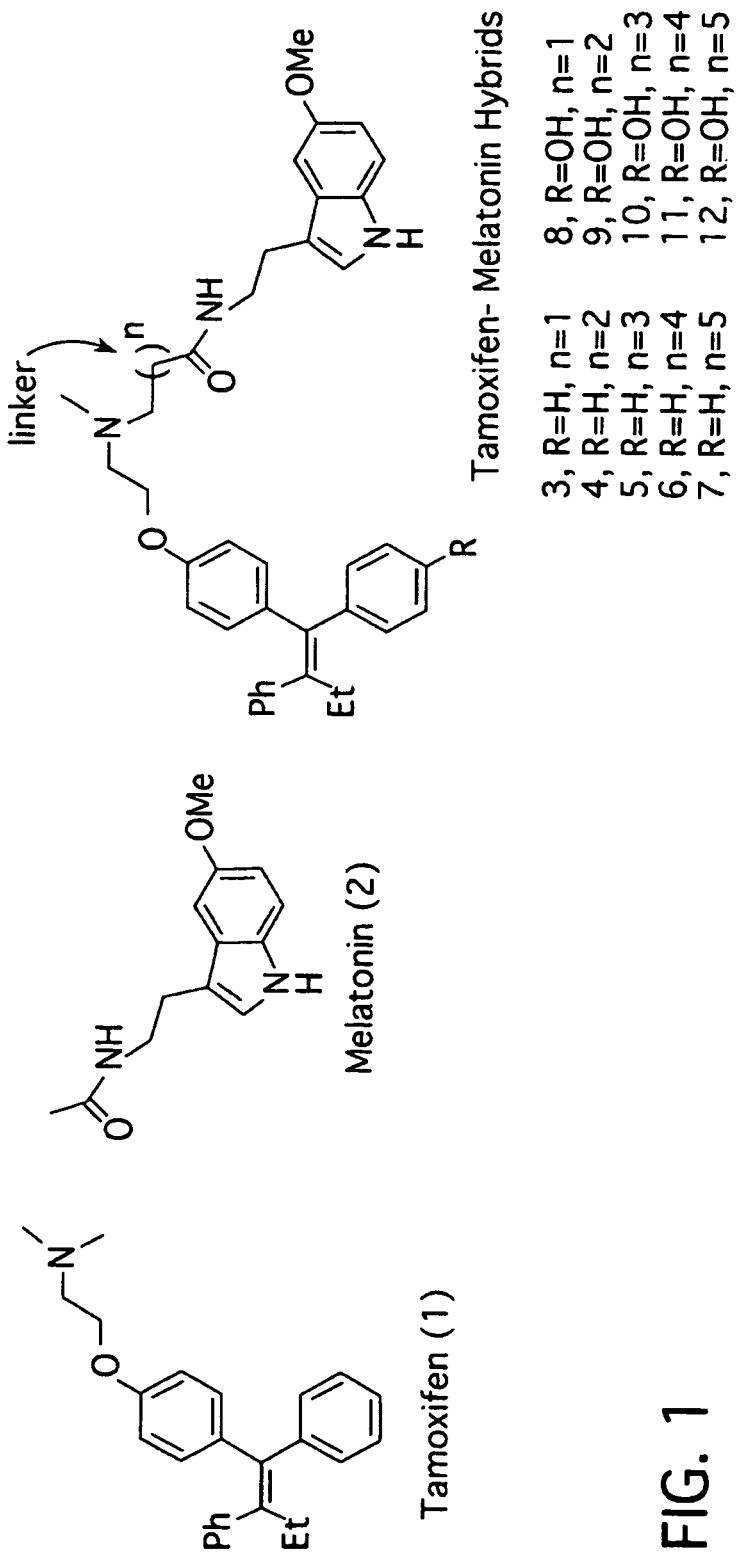
FIG. 1 is chemical formula drawing showing the structures for tamoxifen, melatonin and a hybrid ligand of tamoxifen and melatonin or 4-hydroxytamoxifen and melatonin, linked by a $C_2$-$C_6$ alkyl linker.

The present invention is a particularly constructed tamoxifen-melatonin hybrid ligand that gives new and unexpectedly improved results in the prevention and treatment of cancer, particularly breast cancer. The hybrid ligand comprises either tamoxifen or 4-hydroxytamoxifen and also melatonin, with the tamoxifen or 4-hydroxytamoxifen and melatonin all being linked by a substituted or unsubstituted $C_2$-$C_6$ alkyl linker between the tamoxifen amine and the carbonyl of melatonin. The chemical formula of the present hybrid ligand, including the 4-hydroxy and $C_2$-$C_6$ alkyl linker variations, is shown in FIG. 1. The preferred alkyl linker is $C_5$.

Figure 2:
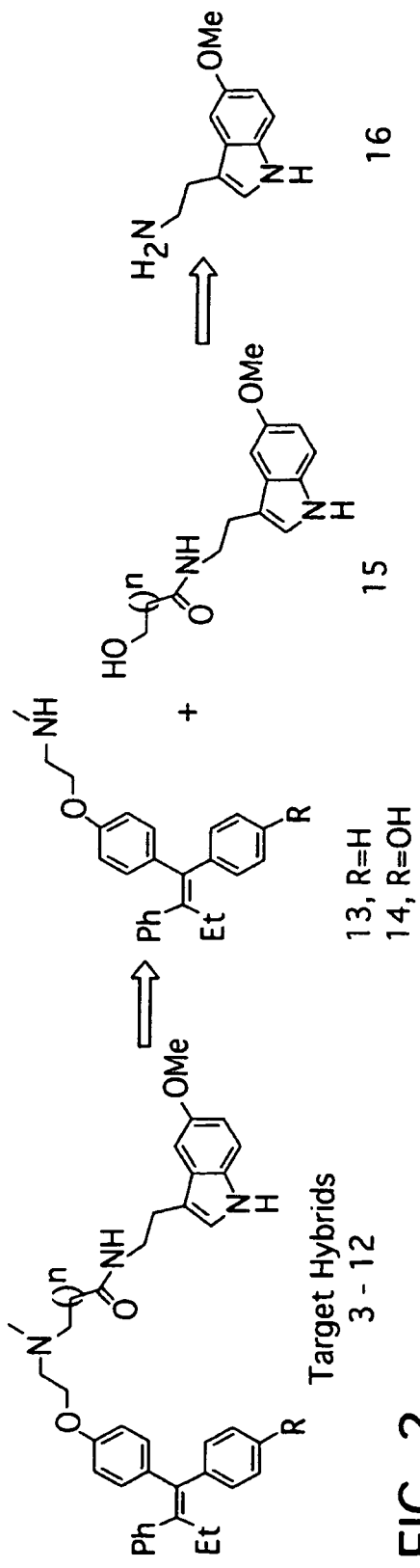
FIG. 2 is a chemical formula drawing showing chemical synthesis structures displayed in retrosynthetic progression.

Synthesis of the present hybrid may be accomplished by means known in the organic chemistry arts. One way to synthesize the hybrid (shown in retrosynthetic progression in FIG. 2) is to convert either tamoxifen or 4-hydroxytamoxifen to its corresponding secondary amine and to react it with an indole alcohol derivative of melatonin (shown as compound 15 in FIG. 2). An important human metabolite of tamoxifen is 4-hydroxytamoxifen, and the ligand may be synthesized of either tamoxifen or 4-hydroxytamoxifen. The reaction may be either a reductive amination known in the art (which requires oxidizing the alcohol of compound 15 of FIG. 2 to the corresponding aldehyde) or an alkylation strategy which requires the alcohol functionality of compound 15 of FIG. 2 to be converted into a leaving group. Although at least some of the indole alcohol derivatives of melatonin shown in FIG. 2 are already known at this writing, indole alcohol derivatives of melatonin may be prepared by acylation of commercially available 5-methoxytryptamine, according to the ordinary skill of the art.

The solubility of the present tamoxifen-melatonin hybrid ligand in water is relatively low. The ligand may be formulated as are other similarly low-water-soluble active agents in suspensions, microsuspensions, in solutions with appropriate solubilizers, and may be formulated into tablets, capsules, caplets, powders, buccal, sublingual and transdermal dosage forms by means known in the art. Generally speaking, formulations that have been or are suitable for tamoxifen are similarly suitable for the present hybrid ligand. For example, the designed quantity of the hybrid ligand may be formulated with up to 95% ethyl alcohol together with isopropyl myristate, hydroxypropylcellulose (or other typical pharmaceutical alkylcellulose excipient) and phosphate buffer to create a topical gel formulation, or the hybrid ligand may be formulated into an oral dosage form by admixing it with typical tableting excipients and diluents known in the art. The present hybrid ligand may be administered by a variety of routes of administration, including but not limited to oral, parenteral, intramuscular, intratumoral, transdermal, buccal, sublingual or other transmucosal. For compliance reasons, the oral route of administration is preferred, although it should be borne in mind that 4-hydroxytamoxifen is the predominant and highly active human metabolite of tamoxifen. Therefore, particularly with the 4-hydroxytamoxifen-melatonin hybrid ligand, non-oral routes of administration are preferred so as to avoid the hepatic first pass effect and to capitalize on the high activity of the metabolite form of tamoxifen.

A typical dose of the present hybrid ligand is on the order of delivering the equivalent of up to about 40 mg per day per patient of tamoxifen per se for treatment and up to about 20 mg per day of tamoxifen per se for prevention of cancer. Because of the relative molecular weights of the components of the hybrid ligands, hybrid ligand containing 20 mg of tamoxifen moiety weighs about 81 g. Therefore, dosing of the present hybrid ligand to a patient should be in the area of 1.80 mg hybrid ligand for prevention of cancer, more preferably 5-80 mg, and most preferably 20-80 mg of hybrid ligand (all amounts are per day per average sized patient). For treatment of cancer, about 1-165 mg hybrid ligand per day, more preferably about 20-160 mg per day and most preferably about 80-160 mg hybrid ligand per day per patient should be administered. Dosing should be adjusted pro rata for smaller or larger patients by weight. Preferably, the hybrid ligand dose is administered at bedtime or at night.

The following Examples are illustrative and are not intended to be limiting.

Example 1

The pharmacology of the hybrid ligand disclosed herein was tested as follows. A tamoxifen-melatonin hybrid ligand (compound 6 of FIG. 1) containing an unsubstituted alkyl linker having five carbons was prepared and administered to wild-type mice (FVB/n strain). Subcutaneous injection of the present hybrid ligand ("MTHL") into ovariectomized, wild-type female mice resulted in similar effects on mammary estrogen-regulated genes (i.e., lactoferrin and progesterone receptor) as detected with tamoxifen or melatonin alone or with co-administration of the separate therapies. These data suggest that the present MTHL displays similar pharmacology as the individual ligands in mammary tissue. The ability of the hybrid ligand to induce effects in mouse tissues distant from the injection site also demonstrates that the hybrid ligand is bioavailable. However, the hybrid ligand produced effects in the uterus distinct from those produced with the co-administration of the separate therapies. Previous studies with melatonin or tamoxifen alone were done in MMTV/neu mice. MMTV/neu mice spontaneously develop HER2/neu mammary cancer beginning at 5 months of agent and have a maximal incidence of >90% after 14 months of age. In this mouse model, tamoxifen and melatonin alone can influence mammary tumor development, growth and/or metastatic progression.

Figure 3:
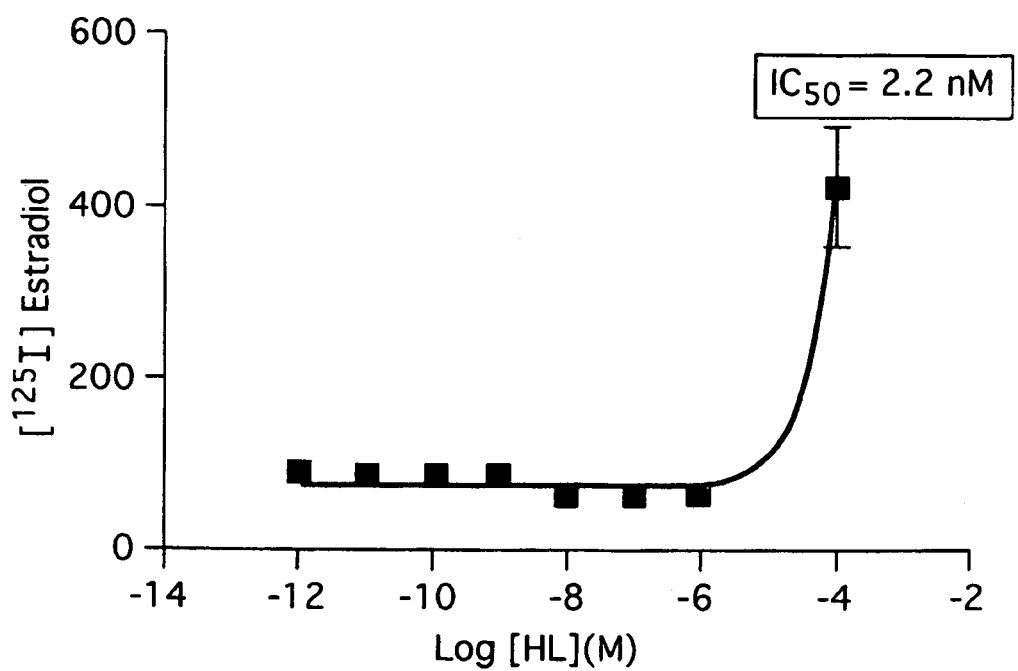
FIG. 3 is a line graph entitled, "Competition of HL (Hybrid Ligand) for $[^{125}I]$ Estradiol Binding to ERs (Estrogen Receptors) Expressed in Mouse Uterus, as discussed in Example 1 below.
Figure 4A:
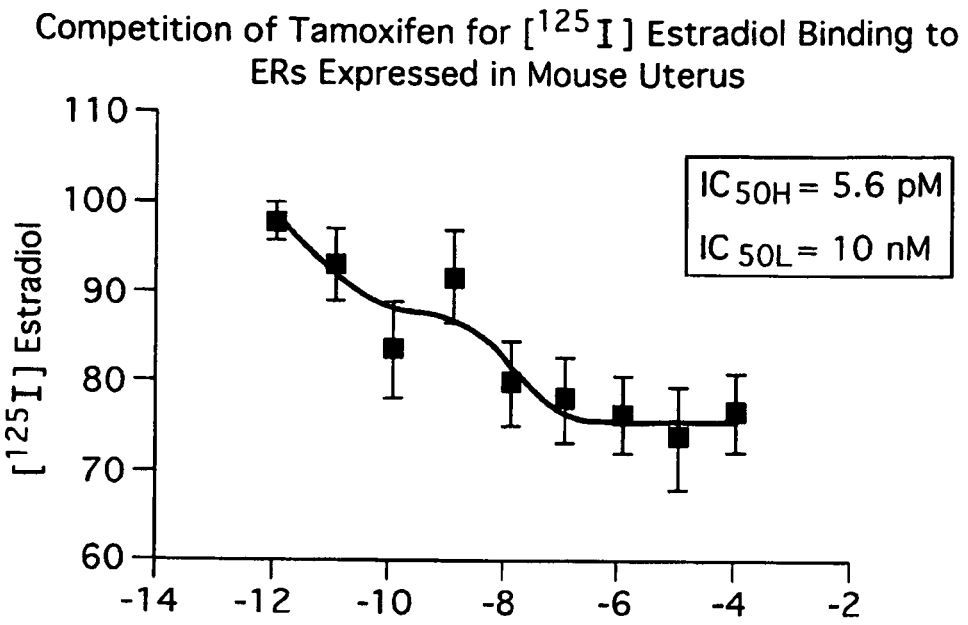
Figure 4B:
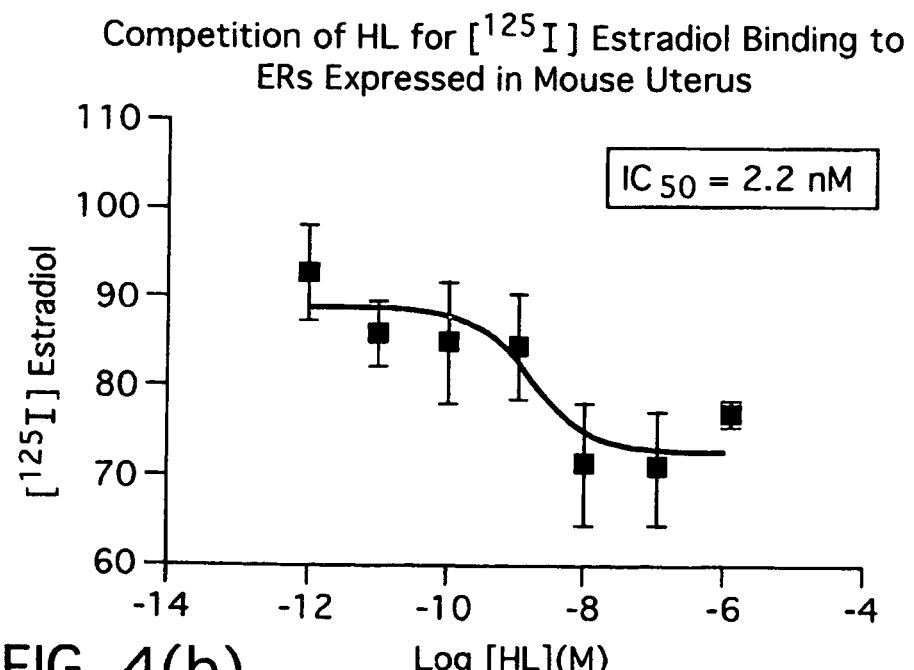
Figure 4C:
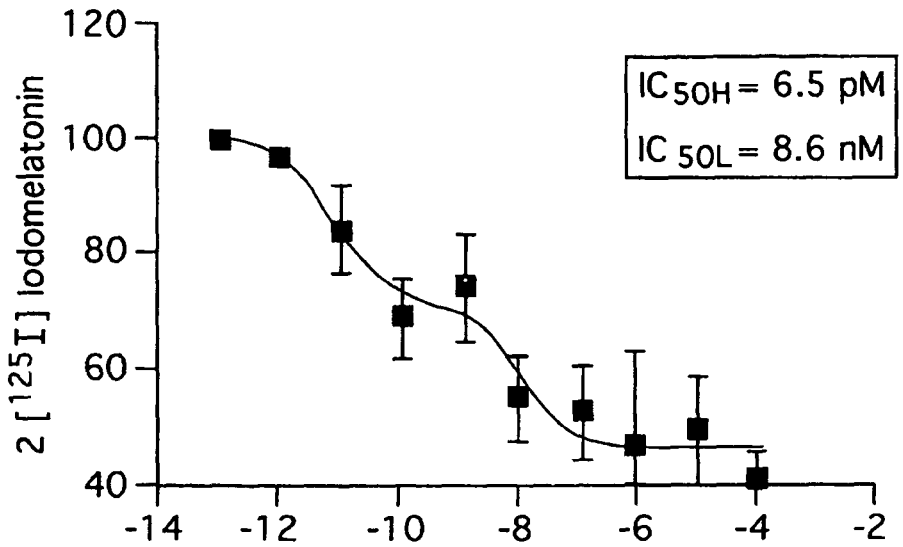
Figure 4D:
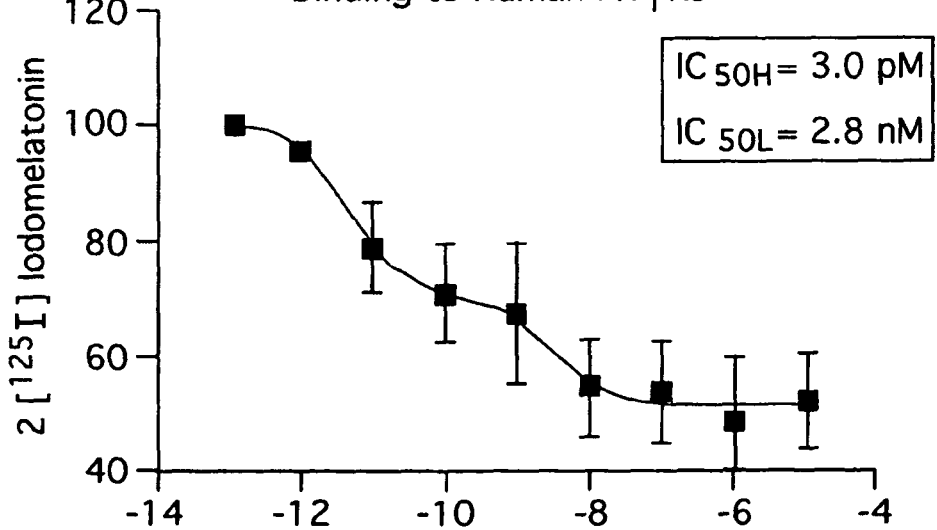
Figure 5A:
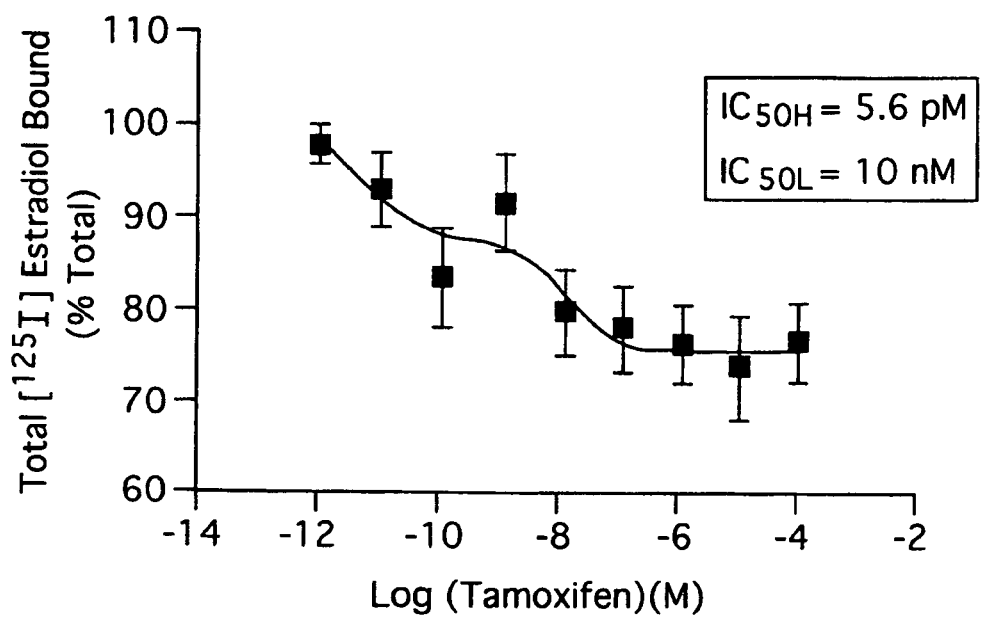
Figure 5A:
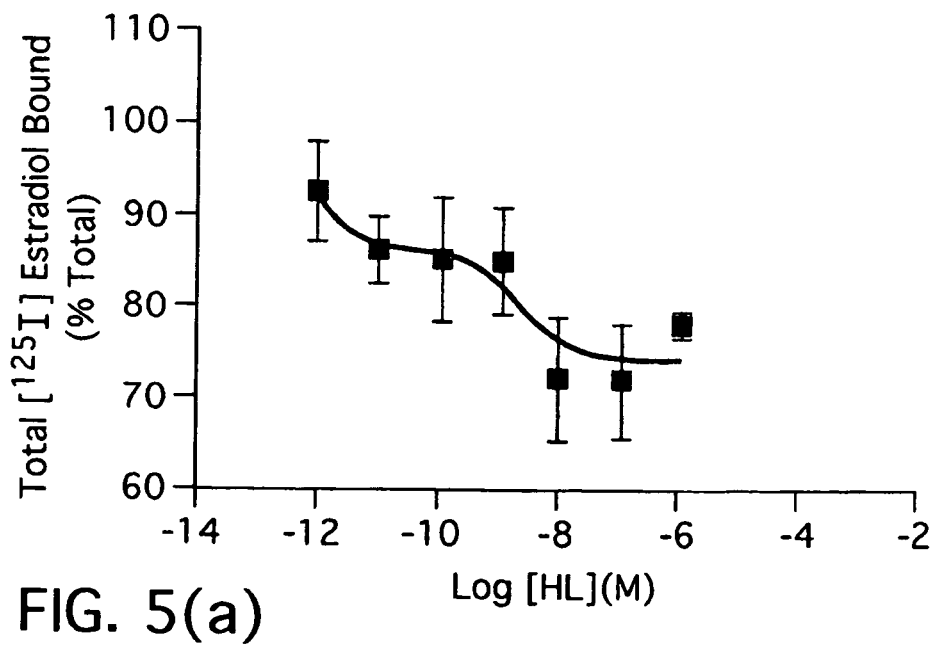
Figure 5B:
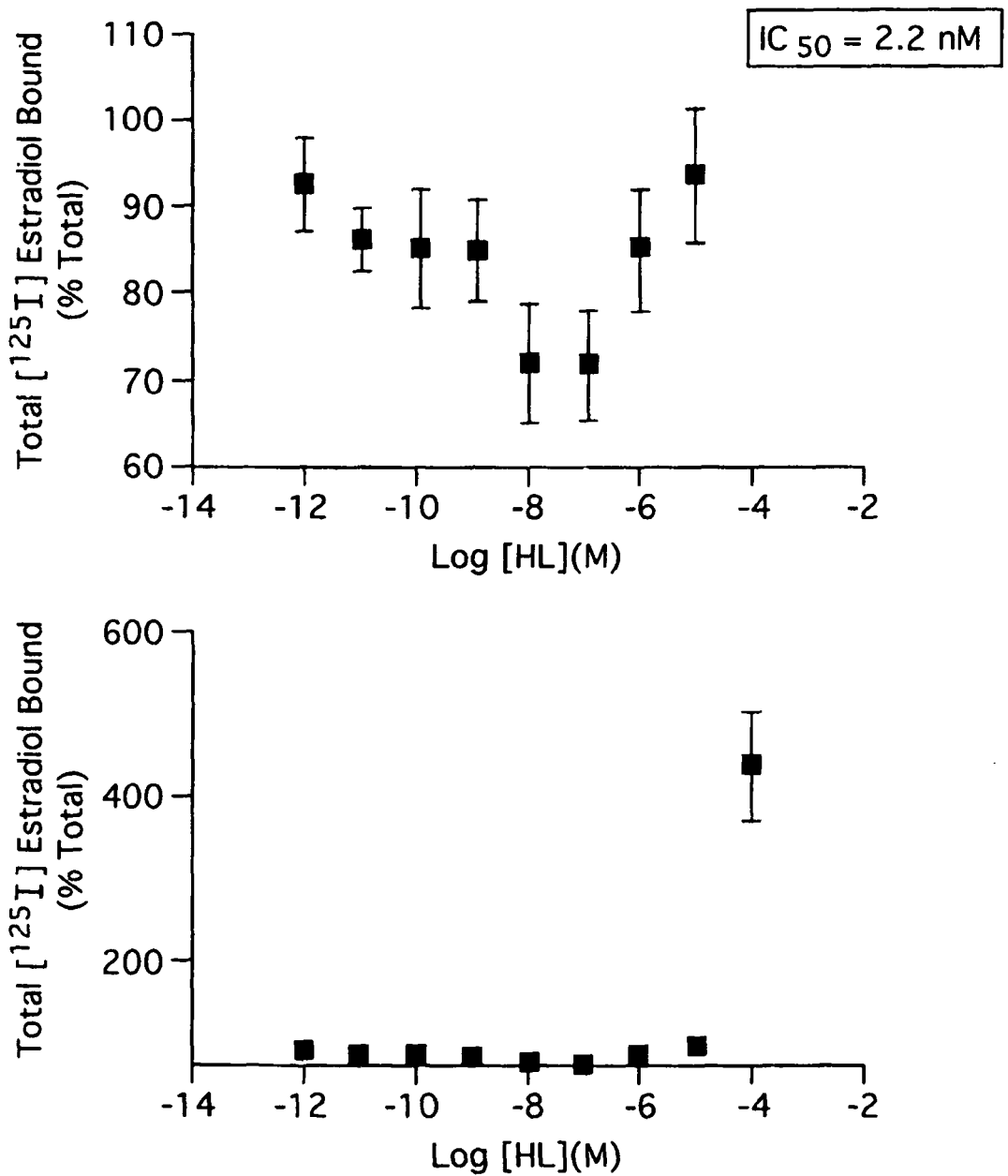
Figure 5C:
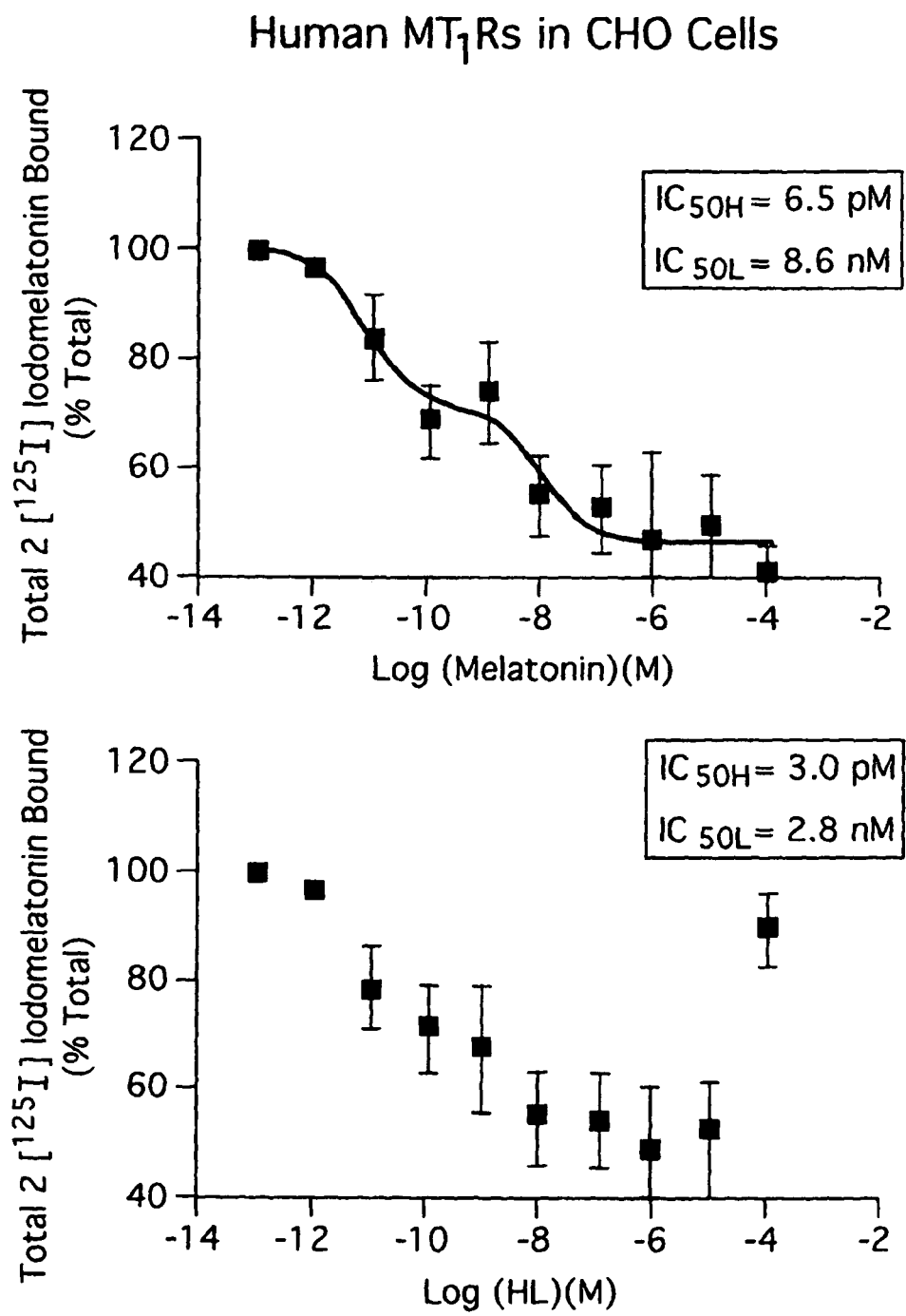

The affinity of the hybrid ligand was tested in vitro. Our data show that melatonin-tamoxifen hybrid ligand (MTHL) binds with equal affinity to estrogen receptors (ERs) expressed in mouse uterus or to $MT_1$ receptors ($MT_1R$) expressed in recombinant model systems. In addition to all of the above, at hybrid ligand concentrations from 1 picomolar to 1 micromolar, the inventors observed the expected concentration dependent inhibition of estradiol binding. However, at greater than 1 micromolar concentration of the hybrid ligand in mice, unique results were achieved as follows and the results are believed to show positive effects in the body. The unique results amounted to enhanced binding $[^{125}I]$ estradiol binding to the estrogen receptor by an increase of 437%, compared to baseline 100% which is $[^{125}I]$ estradiol binding without a competing ligand's being present. See FIG. 3. Also, FIGS. 4 and 5 set forth new data on the binding of $[^{125}I]$ melatonin at the human MT1 receptor at concentrations greater than 10 micromolar. This, too, reverses the trend of inhibition of $[^{125}I]$ melatonin binding by the hybrid ligand to an increase in $[^{125}I]$ melatonin binding similar to baseline (compare 53% of total of $[^{125}I]$ melatonin bound to the MT1 receptor in the presence of 10 micromolar hybrid ligand to 90% of total of $[^{125}I]$ melatonin bound in the presence of the hybrid ligand.)

Example 2

New and unexpected results are apparent from administration of the inventive hybrid ligand, judging from in vivo studies in mice, because although the hybrid ligand creates the desired binding and anti-cancer effect in mammary tissues, to prevent or to treat breast cancer, the hybrid ligand does not create hyperproliferation of uterine tissue as does tamoxifen per se when administered alone. More particularly, when ovariectomized FVB/n mice are given tamoxifen alone, their uterine weights increase. Even when the same type mice are treated with tamoxifen and melatonin together, the uterine weights (undesirably) increase. However, when the present inventive hybrid ligand is administered, the uterine weight was not significantly different than control, even though the hybrid ligand still had the desired effect on the mammary tissues in the same mice. These conclusions are supported in the following summarized data. Uterotrophic assays were performed on FVB/n OVX mice to assess the in vivo actions of the hybrid ligand described in Example 1 (200 µg/kg s.c daily for 3 days) compared to the control agents (vehicle, 150 µg/kg tamoxifen, 63 µg/kg melatonin, 20 µg/kg $E_2$ daily for 3 days). On day 4, uterine weight/body weight for the mice receiving hybrid ligand was not significantly different than control (control 0.57±0.4 vs. hybrid ligand 0.77±0.12 mg/g), unlike tamoxifen alone (1.20±0.05 mg/g, p<0.05), tamoxifen+melatonin (unlinked; 1.10±0.04 mg/g, p<0.05), and $E_2$ (2.45±0.08 mg/g, p<0.05). Data from the mammary tissue indicates that the hybrid ligand is bioavailable due to its ability to stimulate expression of the progesterone receptor (PR) RNA levels in mammary tissue similar to tamoxifen and unlinked tamoxifen+melatonin, and all 3 groups were significantly different than the control (vehicle) and melatonin alone (n=4; data not shown). These data demonstrate both that the hybrid ligand creates biological activity and that the hybrid ligand results in reduced uterine stimulation after short-term administration. This result—desired effect in mammary tissue without undesired effect in uterine tissue—evidences new and unexpected results with the present hybrid ligand.

The invention claimed is:

1. A pharmaceutically active agent consisting essentially of a hybrid ligand of tamoxifen and melatonin linked by a 2-6 carbon alkyl linker conjoining said tamoxifen and said melatonin via a covalent linkage between an amino moiety of said tamoxifen and a hydroxylamino moiety of said melatonin.

2. The hybrid ligand according to claim 1 wherein said tamoxifen is a 4-hydroxytamoxifen moiety.

3. The hybrid ligand according to claim 1 wherein said alkyl linker is substituted or unsubstituted and contains 5 carbon atoms.

4. A pharmaceutical formulation consisting essentially of a hybrid ligand of tamoxifen and melatonin linked by a 2-6 carbon unsubstituted alkyl linker conjoining said tamoxifen and said melatonin via a covalent linkage of an amino moiety of said tamoxifen and a hydroxylamino moiety of said melatonin, and at least one pharmaceutically acceptable excipient.

5. The pharmaceutical formulation according to claim 4 wherein said tamoxifen is 4-hydroxytamoxifen.

* * * * *